United States Patent
Laufer et al.

(10) Patent No.: US 6,835,200 B2
(45) Date of Patent: Dec. 28, 2004

(54) METHOD AND DEVICES FOR TISSUE RECONFIGURATION

(75) Inventors: Michael D. Laufer, Menlo Park, CA (US); Jeffrey C. Cerier, Franklin, MA (US); Amos Cruz, Franklin, MA (US); Jonathan O'Keefe, Scituate, MA (US); Richard Andrews, Lincoln, RI (US); Vincent A. Puicci, Jr., Spencer, MA (US); Michael Barenboym, Ashland, MA (US); Neal H. Marshall, Bolton, MA (US); Randal B. Chinnock, Sturbridge, MA (US)

(73) Assignee: ndo surgical. Inc., Mansfield, MA (US)

( * ) Notice: Subject to any disclaimer, the term of this patent is extended or adjusted under 35 U.S.C. 154(b) by 0 days.

(21) Appl. No.: 10/197,574

(22) Filed: Jul. 18, 2002

(65) Prior Publication Data

US 2003/0055442 A1 Mar. 20, 2003

Related U.S. Application Data

(63) Continuation-in-part of application No. 09/859,579, filed on May 18, 2001, which is a continuation-in-part of application No. 09/520,273, filed on Mar. 7, 2000, now Pat. No. 6,663,639, and a continuation-in-part of application No. 09/519,945, filed on Mar. 7, 2000, now Pat. No. 6,506,196, which is a continuation-in-part of application No. 09/574,424, filed on May 19, 2000, now Pat. No. 6,494,888, application No. 10/197,574.

(60) Provisional application No. 60/306,652, filed on Jul. 18, 2001, and provisional application No. 60/140,492, filed on Jun. 22, 1999.

(51) Int. Cl.[7] ............................................. A61B 17/08

(52) U.S. Cl. ...................................... 606/153; 606/139

(58) Field of Search ................................. 606/153, 139, 606/144, 148, 150, 205–210, 219–221, 232

(56) References Cited

U.S. PATENT DOCUMENTS

| | | | |
|---|---|---|---|
| 3,470,875 A | 10/1969 | Johnson |
| 3,551,987 A | 1/1971 | Wilkinson |
| 3,638,653 A | 2/1972 | Berry |
| 3,842,840 A | 10/1974 | Schweizer |

(List continued on next page.)

FOREIGN PATENT DOCUMENTS

| | | |
|---|---|---|
| EP | 0 480 428 | 4/1992 |
| EP | 0 576 265 | 12/1993 |
| EP | 0 646 356 A2 | 4/1995 |

(List continued on next page.)

OTHER PUBLICATIONS

International Search Report dated Oct. 22, 2003.
Bancewicz et al., "Held pressure, anatomy of the cardia and gastro–o+A25esophageal reflux", Journal of Surgery, 1995, vol. 82, p. 943–947.
The Americal journal of gastroenterology, vol. 91, no. 3, 1996, p. 616–617.

(List continued on next page.)

Primary Examiner—Kevin T. Truong
(74) Attorney, Agent, or Firm—Fish & Richardson P.C.

(57) ABSTRACT

A method includes advancing an apparatus having an elongated member transorally into the stomach. The apparatus includes a distal end effector having first and second members configured to engage tissue. The first and second members are movable relatively toward one another generally in a first plane. The method includes moving the distal end effector relative to the elongated member in the first plane such that the distal end effector is retroflexed out of alignment with the elongated member to position the first and second members for engagement with the tissue. At least one of the first and second members carries a fixation device for fixing engaged portions of tissue together.

15 Claims, 8 Drawing Sheets

U.S. PATENT DOCUMENTS

| | | |
|---|---|---|
| 3,875,648 A | 4/1975 | Bone |
| 3,901,244 A | 8/1975 | Schweizer |
| 3,946,740 A | 3/1976 | Bassett |
| 4,006,747 A | 2/1977 | Kronenthal et al. |
| 4,164,225 A | 8/1979 | Johnson et al. |
| 4,235,238 A | 11/1980 | Ogiu et al. |
| 4,448,194 A | 5/1984 | DiGiovanni et al. |
| 4,471,781 A | 9/1984 | DiGiovanni et al. |
| 4,500,024 A | 2/1985 | DiGiovanni et al. |
| 4,506,670 A | 3/1985 | Crossley |
| 4,573,469 A | 3/1986 | Golden et al. |
| 4,585,153 A | 4/1986 | Failla et al. |
| 4,586,502 A | 5/1986 | Bedi et al. |
| 4,591,085 A | 5/1986 | Di Giovanni et al. |
| 4,605,004 A | 8/1986 | Di Giovanni et al. |
| 4,606,345 A | 8/1986 | Dorband et al. |
| 4,627,437 A | 12/1986 | Bedi et al. |
| 4,696,300 A | 9/1987 | Anderson |
| 4,705,040 A | 11/1987 | Mueller |
| 4,724,840 A | 2/1988 | McVay et al. |
| 4,736,746 A | 4/1988 | Anderson |
| 4,741,336 A | 5/1988 | Failla et al. |
| 4,753,469 A | 6/1988 | Hiscott |
| 4,809,695 A | 3/1989 | Gwathmey |
| 4,887,612 A | 12/1989 | Esser et al. |
| 4,890,615 A | 1/1990 | Caspari et al. |
| 4,935,027 A | 6/1990 | Yoon |
| 5,015,249 A | 5/1991 | Nakao |
| 5,037,433 A | 8/1991 | Wilk et al. |
| 5,088,979 A | 2/1992 | Filipi et al. |
| 5,147,373 A | 9/1992 | Ferzli |
| 5,222,963 A | 6/1993 | Brinkerhoff et al. |
| 5,254,126 A * | 10/1993 | Filipi et al. ................ 606/146 |
| 5,336,263 A | 8/1994 | Ersek |
| 5,346,504 A | 9/1994 | Ortiz et al. |
| 5,356,416 A | 10/1994 | Chu et al. |
| 5,358,508 A | 10/1994 | Cobb |
| 5,364,408 A | 11/1994 | Gordon |
| 5,395,030 A | 3/1995 | Kuramoto et al. |
| 5,403,326 A | 4/1995 | Harrison et al. |
| 5,433,721 A | 7/1995 | Hooven et al. |
| 5,441,507 A | 8/1995 | Wilk |
| 5,447,512 A | 9/1995 | Wilson et al. |
| 5,451,406 A | 9/1995 | Lawin |
| 5,465,894 A | 11/1995 | Clark et al. |
| 5,486,189 A | 1/1996 | Mudry et al. |
| 5,496,331 A | 3/1996 | Xu et al. |
| 5,522,820 A | 6/1996 | Caspari et al. |
| 5,549,618 A | 8/1996 | Fleenor et al. |
| 5,558,665 A | 9/1996 | Kieturakis |
| 5,571,090 A | 11/1996 | Sherts |
| 5,571,116 A | 11/1996 | Bolanos |
| 5,573,496 A | 11/1996 | McPherson et al. |
| 5,624,453 A | 4/1997 | Ahmed |
| 5,626,613 A | 5/1997 | Schmieding |
| 5,645,552 A | 7/1997 | Shertz |
| 5,662,683 A | 9/1997 | Kay |
| 5,665,096 A | 9/1997 | Yoon |
| 5,674,230 A | 10/1997 | Tovey et al. |
| 5,676,674 A | 10/1997 | Bolanos et al. |
| 5,697,940 A | 12/1997 | Chu et al. |
| 5,722,421 A | 3/1998 | Francese et al. |
| 5,725,524 A | 3/1998 | Mulier et al. |
| 5,728,109 A | 3/1998 | Schulze et al. |
| 5,735,861 A | 4/1998 | Peifer et al. |
| 5,741,280 A | 4/1998 | Fleenor |
| 5,749,898 A | 5/1998 | Schulze et al. |
| 5,787,897 A | 8/1998 | Kieturakis |
| 5,792,153 A | 8/1998 | Swain |
| 5,794,948 A | 8/1998 | Swain |
| 5,797,927 A | 8/1998 | Yoon |
| 5,810,855 A | 9/1998 | Rayburn |
| 5,810,882 A | 9/1998 | Bolduc et al. |
| 5,814,054 A | 9/1998 | Kortenbach et al. |
| 5,826,776 A | 10/1998 | Schulze et al. |
| 5,846,254 A | 12/1998 | Schulze et al. |
| 5,853,409 A | 12/1998 | Swanson et al. |
| 5,855,311 A | 1/1999 | Hamblin et al. |
| 5,887,594 A | 3/1999 | LoCicero, III et al. |
| 5,893,592 A | 4/1999 | Schulze et al. |
| 5,897,562 A | 4/1999 | Bolanos et al. |
| 5,901,895 A | 5/1999 | Heaton et al. |
| 5,958,444 A | 9/1999 | Wallace |
| 5,984,932 A | 11/1999 | Yoon |
| 5,993,466 A | 11/1999 | Yoon |
| 6,009,877 A | 1/2000 | Edwards |
| 6,051,003 A | 4/2000 | Chu et al. |
| 6,059,798 A | 5/2000 | Tolkoff |
| 6,067,990 A | 5/2000 | Kieturakis |
| 6,083,202 A | 7/2000 | Smith |
| 6,086,600 A | 7/2000 | Kortenbach |
| 6,086,603 A | 7/2000 | Termin |
| 6,098,629 A | 8/2000 | Johnson |
| 6,113,609 A | 9/2000 | Adams |
| 6,129,761 A | 10/2000 | Hubbell |
| 6,152,935 A | 11/2000 | Kammerer |
| 6,159,146 A | 12/2000 | El Gazayerli |
| 6,179,840 B1 | 1/2001 | Bowman |
| 6,221,084 B1 | 4/2001 | Fleenor |
| 6,258,064 B1 | 7/2001 | Smith et al. |
| 6,352,503 B1 | 3/2002 | Matsui et al. |
| 6,387,104 B1 | 5/2002 | Pugsley, Jr. et al. |
| 6,551,315 B2 | 4/2003 | Kortenbach et al. |
| 6,569,085 B2 | 5/2003 | Kortenbach et al. |
| 6,569,105 B1 | 5/2003 | Kortenbach et al. |
| 6,579,301 B1 | 6/2003 | Bales et al. |
| 6,632,227 B2 | 10/2003 | Adams |
| 6,645,201 B1 | 11/2003 | Utley et al. |
| 6,660,301 B1 | 12/2003 | Vogel et al. |
| 6,663,639 B1 | 12/2003 | Laufer et al. |
| 6,666,848 B2 | 12/2003 | Stone |
| 6,669,713 B2 | 12/2003 | Adams |
| 2001/0049537 A1 | 12/2001 | Kortenbach |
| 2001/0056282 A1 | 12/2001 | Sonnenschein |
| 2002/0063143 A1 | 5/2002 | Adams et al. |
| 2002/0068945 A1 | 6/2002 | Sixto, Jr. et al. |
| 2002/0068946 A1 | 6/2002 | Kortenbach |
| 2002/0078967 A1 | 6/2002 | Sixto, Jr. et al. |
| 2002/0082621 A1 | 6/2002 | Schurr |
| 2002/0138086 A1 | 9/2002 | Sixto, Jr. et al. |
| 2002/0173786 A1 | 11/2002 | Kortenbach et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2002/0198549 A1 | 12/2002 | Sixto, Jr. et al. |
| 2003/0019905 A1 | 1/2003 | Adams et al. |
| 2003/0036679 A1 | 2/2003 | Kortenbach et al. |
| 2003/0188755 A1 | 10/2003 | Milbocker |
| 2003/0191478 A1 | 10/2003 | Kortenbach et al. |
| 2003/0192558 A1 | 10/2003 | Durgin |
| 2003/0192559 A1 | 10/2003 | Durgin |
| 2003/0195387 A1 | 10/2003 | Kortenbach et al. |
| 2003/0195509 A1 | 10/2003 | Edwards et al. |
| 2003/0196670 A1 | 10/2003 | Durgin |
| 2003/0199731 A1 | 10/2003 | Silverman et al. |
| 2003/0208209 A1 | 11/2003 | Gambale et al. |
| 2003/0208211 A1 | 11/2003 | Kortenbach |
| 2003/0216754 A1 | 11/2003 | Kraemer et al. |
| 2003/0220657 A1 | 11/2003 | Adams |

| | | | |
|---|---|---|---|
| 2003/0220660 A1 | 11/2003 | Kortenbach et al. | |
| 2003/0236535 A1 | 12/2003 | Onuki et al. | |
| 2003/0236536 A1 | 12/2003 | Grigoryants et al. | |

FOREIGN PATENT DOCUMENTS

| | | |
|---|---|---|
| EP | 0975263 | 10/2003 |
| FR | 2 768 324 | 3/1999 |
| WO | WO 99/22649 | 5/1999 |
| WO | WO99/60931 | 12/1999 |
| WO | WO 00/35529 | 12/2000 |
| WO | WO 00/78227 | 12/2000 |
| WO | 00/78229 | 12/2000 |
| WO | WO00/78229 | 12/2000 |
| WO | WO 02/24080 | 3/2002 |
| WO | WO 02/40081 | 5/2002 |
| WO | WO 02/45603 | 6/2002 |
| WO | WO02/094341 | 11/2002 |
| WO | WO 03/000115 | 1/2003 |
| WO | WO 03/004087 | 1/2003 |
| WO | WO 03/007796 | 1/2003 |
| WO | WO 03/015604 | 2/2003 |
| WO | WO 03/082359 | 10/2003 |
| WO | WO 03/090633 | 11/2003 |
| WO | WO 03/092498 | 11/2003 |
| WO | WO 03/092509 | 11/2003 |
| WO | WO 03/094800 | 11/2003 |
| WO | WO 03/098885 | 11/2003 |
| WO | WO 03/099137 | 12/2003 |
| WO | WO 03/099139 | 12/2003 |
| WO | WO 03/099140 | 12/2003 |
| WO | WO 03/099376 | 12/2003 |
| WO | WO03/105917 | 12/2003 |
| WO | WO2004/000129 | 12/2003 |

OTHER PUBLICATIONS

Donahue et al., "Endoscopic control of gastro–esophageal reflux11:14 AM status report", World Journal of Surgery, 16: 343–346, 1992.

International Search Report dated Oct. 16, 2000.

Carvalho PJPC et al., Fibrosis of gastric cardia after endoscopic sclerosis. Mechanism for control of experimental reflux? *Am Surg* Mar. 1990;56(3):163–6.

Contractor QQ et al., Endoscopic esphagitis and gastroesophageal flap valve. *J Clin Gastroenterol* Apr. 1999; 28 (3):233–7.

Hill LD and Kozarek RA, The gastroesophageal flap valve. *J Clin Gastroenterol* Apr. 1999:28(3):194–7.

Hill LD et al., Antireflux surgery. A surgeon's look. *Gastroenterol Clin North Am* Sep. 1990:19(3):745–75.

Hill LD et al., The gastroesophageal flap valve: in vitro and in vivo observations. *Gastrointest Endosc* Nov. 1996;44(5):541–7.

Hill LD, Intraoperative measurement of lower esophageal sphincter pressure. *J Thorac Cardiovasc Surg* Mar. 1978;75(3):378–82.

Hill LD, Mythis of the esophagus. *J Thorac Cardivasc Surg* Jul. 1989;98(1):1–10.

Ismail T. et al., Yield pressure, anatomy of the cardia and gastro–oesophageal reflux. *Br J Surg* Jul. 1995;82(7):943–7.

Kadirkamanathan SS et al., An ambulant porcine model of acid reflux used to evaluate endoscopic gastroplasty. *Gut* Jun. 1999;44(6):782–8.

Kadirkamanathan SS et al., Antireflux operations at flexible endoscopy using endoluminal stitching techniques: an experimental study. *Gastrointest Endosc* Aug. 1996;44(2):133–43.

Mason RJ et al., A new intraluminal antigastroesophageal reflux procedure in baboons. *Gastrointest Endosc* Mar. 1997;45(3):283–90.

McGouran RC et al., Does measurement of yield pressure at the cardia during endoscopy provide information on the function of the lower oestophageal sphincter mechanism? *Gut* Mar. 1988;29(3):275–8.

McGouran RC et al., Is yield pressure at the cardia increased by effective fundoplication? *Gut* Oct. 1989;30(10):1309–12.

O'Connor KW et al., An experimental endoscopic technique for reversing gastroesophageal reflux in dogs by injecting inert material in the distal esophagus. *Gastrointest Endosc* Oct. 1984;30(5):275–80.

Rupp TH and Lehman GA, Endoscopic antireflux techniques. Endoluminal and lapaoscopic. *Gastrointest Endosc Clin N Am* Apr. 1994;4(2):353–68.

Shafik A., Intraesophageal Polytef injection for the treatment of reflux esophagitis. *Surg Endosc* Mar. 1996;10(3):329–31.

Slim K et al., Intraoperative esophageal manometry and fundoplications: prospective study. *World J Surg* Jan. 1996;20(1):55–9.

Thor KBA et al., Reappraisal of the flap valve mechanism in the gastroesophageal junction. A study of a new valvuloplasty procedure in cadavers. *Acta Chir Scand* Jan. 1987;153(1):25–8.

Boerema, M.D. , "Hiatus hernia: Repair by right–sided, subhepatic, anterior gastropexy," *Surgery*, 65:884–893 (1969).

Cecconello, "Esophagogastric Anastomosis with Valvuloplasty: An Experimental Study," *International Surgery*, 67:121–124 (1982).

Collis, M.D., "Surgical Control of Reflux in Hiatus Hernia," *The American Journal of Surgery*, 115:465–471 (1968).

Collis, M.D., "An Operation for Hiatus Hernia with Short Esophagus," *The Journal of Thoracic Surgery*, 34:768–778 (1957).

Cuschieri, et al. , "Multicenter prospective evaluation of laparoscopic antireflux surgery," *Surgical Endoscopy*, 7:505–510 (1993).

DeMeester, M.D. et al., "Nissen Fundoplication for Gastroesophageal Reflux Disease," *Annals of Surgery*, 204:9–20 (1986).

Donahue, M.D., et al., "Endoscopic Control of Gastro–Esophageal Reflux: Status Report," *World Journal of Surgery*, 16:343–346 (1992).

Donahue, M.D., et al., "Endoscopic sclerosis of the gastic cardia for prevention of experimental gastroesophageal reflux," *Gastrointestinal Endoscopy*, 36:253–256 (1990).

Falk, et al., "Laparoscopic Fundoplication: A preliminary report of the technique and postoperative care," *Aust. N.Z. J. Surgery*, 62:969–972 (1992).

Hill, et al., "Surgery for Peptic Esophageal Stricture," 139–147.

Hill, M.D., "An Effective Operation for Hiatal Hernia: An Eight Year Appraisal," *Annals of Surgery*, 166:681–692 (1967).

Hill, et al., "The Esophagus, Medical and Surgicial Management," *WB Saunders Co.*, 135–8 (1988).

Hinder, et al. "The Surgical Option for Gastroesophageal Reflux Disease," Symposium on Gastroesophageal Reflux Disease, *Am J Med*, 103:144S–148S (1997).

Ismail, et al., "Yield Pressure: A New Concept in the Evaluation of Gerd?," *AJG*, 91:616–617 (1996).

Jamieson, et al., "The development of surgery for gastro–oesophageal reflux disease," *Surgery of the Oesophagus*, 233–245 (1988).

Jamieson, et al., "Laparoscopic Nissen Fundoplication," *Annals of Surgery*, 220:137–145 (1994).

Janssen, et al., "Prospective randomized comparison of teres cardiopexy and Nissen fundoplication in the surgical therapy of gastro–oesophageal reflux disease," *Br. J.Surg.* 80:875–878 (1993).

Jennings, et al., "A Novel Endoscopic Transgastric Fundoplication Procedure for Gastroesophageal Reflux: An Initial Animal Evaluation," *Journal of Laparoendoscopic Surgery*, 2:207–213 (1992).

Kahrilas, "Gastroesophageal Reflux Disease,"*JAMA*, 276:983–988 (1996).

Kraemer, M.D., et al., "Laparoscopic Hill repair," *Gastrointestinal Endoscopy*, 40:155–159 (1994).

Little, M.D., "Mechanisms of Action of Antireflux Surgery: Theory and Fact," *World Journal of Surgery*, 16:320–325 (1992).

Mason, et al., "Nissen Fundoplication Prevents Shortening of the Sphincter During Gastric Distention," *Arch Surg.*, 132:719–726 (1997).

McGouran, M.D., et al., "A laser–induced scar at the cardia increases the yield pressure of the lower esophageal sphincter," *Gastrointestinal Endoscopy*, 36:439–443 (1990).

McKernan, "Laparoscopic repair of gastroesophageal reflux disease," *Surgical Endoscopy*, 8:851–856 (1994).

Nathanson, et al., "Laparoscopic Ligamentum teres (round ligament) cardiopexy," *Br. J. Surg.*, 78:947–951 (1991).

Nissen, "Eine einfache Operation zur Beeinflussung der Refluxoesophagitis," *Journal Suisee De Medecine*, 590–592 (1956).

O'Connor, et al., "Endoscopic placement of collagen at the lower esophageal sphincter to inhibit gastroesophageal reflux: a pilot study of 10 medically intractable patients," *Gastrointestinal Endoscopy*, 34:106–112 (1988).

Pedinielli, "Traitement Chirurgical de la Herinie Hiatale Par La Technique du Collet", *Ann. Chir.*, 18:1461–1474 (1964). (English Abstract).

Polk, et al. "Hiatol Hernia and Esophagitis: A survey of indications for operation and technic and results of fundoplication," *Ann. Surg.*,173:775–781 (1971).

Rampal, et al., "Technique Chirurgicale, Traitement des hernies hiatales et du reflux aesophagien par la cardio–pexie avec le ligament round de foie," *La Presse Medicale*, 75:617–619 (1967).

Rich, "Simple GERD Treatment Offers New Alternative, "(www.medicalpost.com website), Mar. 1999.

Singh, et al., "Evaluation of the Endoscopic Suturing System in the Treatment of GERD," *DDW*, May 16–19, 1999.

Skinner, et al., "Surgical management of esophageal reflux and hiatus hernia," *Journal of Thoracic and Cardiovascular Surgery*, 53:33–54 (1967).

Starling, et al. Assessment of the Angelchik Prosthesis for Treatment of Symptomatic Esophageal Reflux, *World J. Surg.* 11, 350–355 (1987).

Tocornal, M.D., et al., "A mucosol flap valve mechanism to prevent gastroesophageal reflux and esophagitis," *Surgery*, 64:519–523 (1968).

Wang, et al., "A new anti–flux procedure: cardiac oblique invagination," *Chung Hua Wai Ko Tsa Chih*, Feb.; 33 (2) 73–5 (1995). (English Abstract).

Watson, et al., "Comparison of anterior, posterior and total fundoplication using a viscera model," *Diseases of the Esophagus*, 10: 110–114 (1997).

Westbrook, et al., "Posterior Surgical Approaches to the Rectum," *Annals of Surgery*, 195:677–691 (1982).

U.S. patent application Publication US 2001/0056282 A1, Dec. 27, 2001.

U.S. patent application Publication US 2002/0068946 A1, Jun. 6, 2002.

U.S. patent application Publication US 2002/0082621 A1, Jun. 27, 2002.

* cited by examiner

METHOD AND DEVICES FOR TISSUE RECONFIGURATION

This application claims the priority of U.S. provisional application Ser. No. 60/306,652, filed Jul. 18, 2001, which is hereby incorporated by reference in its entirety.

This application is a continuation-in-part of copending application U.S. Ser. No. 09/859,579, filed May 18, 2001, entitled TISSUE RECONFIGURATION, which is a continuation-in-part of application U.S. Ser. No. 09/574,424, filed May 19, 2000, now U.S. Pat. No. 6,494,888, entitled TISSUE RECONFIGURATION, which is a continuation-in-part of application U.S. Ser. No. 09/520,273, filed Mar. 7, 2000, now U.S. Pat. No. 6,663,639, entitled METHODS AND DEVICES FOR TISSUE RECONFIGURATION, and is a continuation-in-part of U.S. Ser. No. 09/519,945, filed Mar. 7, 2000, now U.S. Pat. No. 6,506,196 entitled DEVICE AND METHOD FOR CORRECTION OF A PAINFUL BODY DEFECT, which claim priority from provisional application U.S. Ser. No. 60/140,492, filed Jun. 22, 1999, this application Ser. No. 10/197,574 entitled STOMACH ELEVATOR METHOD AND DEVICE, all hereby incorporated by reference in their entirety.

BACKGROUND OF THE INVENTION

Brief Description of the Related Art

This invention relates to devices and methods for treating gastroesophageal reflux disease, and more particularly, the invention relates to a minimally invasive device and method for creating and fixating a fold of tissue at or near the junction of the esophagus and the stomach.

Gastroesophageal reflux disease (GERD) is a common upper-intestinal disorder in which contents of the stomach flow inappropriately from the stomach into the esophagus. Backflow of gastric contents into the esophagus results when gastric pressure is sufficient to overcome the resistance to flow that normally exists at the gastroesophageal junction (GEJ), or when gravity acting on the contents is sufficient to cause flow through the GEJ. Medication, open surgical procedures, laparoscopic surgical procedures, and endoscopic techniques are known for treating GERD.

SUMMARY OF THE INVENTION

According to one aspect of the invention, a medical instrument includes moveable arms configured for fixating the wall of the stomach to the wall of the esophagus for the treatment of GERD. In one embodiment, the instrument includes a proximal end, a shaft, a retroflexing portion, movable arms, a retractor, and an implant. The movable arms are oriented with respect to the retroflexing portion in a position that allows the stomach wall to be folded against the esophagus wall. In one such embodiment of this instrument the movable arms open and close in the same plane within which the retroflexing portion moves. This configuration is in contrast to certain embodiments of the medical instrument described in the U.S. patent application Ser. No. 09/859,579, entitled "TISSUE RECONFIGURATION," filed May 18, 2001, in which the moveable arms are oriented in a plane rotated 90° from the plane in which the retroflexing portion moves. The mechanism of operation of the medical instrument of the current invention is as is disclosed in the patent applications incorporated by reference and listed above.

According to another aspect of the invention, a method of treatment includes fixating the wall of the stomach to the wall of the esophagus for the treatment of GERD.

According to another aspect of the invention, a method includes advancing an apparatus having an elongated member transorally into the stomach. The apparatus includes a distal end effector having first and second members configured to engage tissue. The first and second members are movable relatively toward one another generally in a first plane. The method includes moving the distal end effector relative to the elongated member in the first plane such that the distal end effector is retroflexed out of alignment with the elongated member to position the first and second members for engagement with the tissue. At least one of the first and second members carries a fixation device for fixing engaged portions of tissue together.

Embodiments of this aspect of the invention may include one or more of the following features. The method includes engaging tissue by moving the first and second members relatively toward one another generally in the first plane. Moving the first and second members engages a first tissue section with a first securing part of the fixation device and a second tissue section with a second securing part of the fixation device. The method includes piercing the tissue with a third member of the distal end effector prior to engaging the tissue with the first and second members.

BRIEF DESCRIPTION OF THE DRAWINGS

The invention will now be described in greater detail with reference to the preferred embodiment illustrated in the accompanying drawings, in which like elements bear like reference numerals, and wherein.

DETAILED DESCRIPTION OF THE PREFERRED EMBODIMENT

Figure 1:
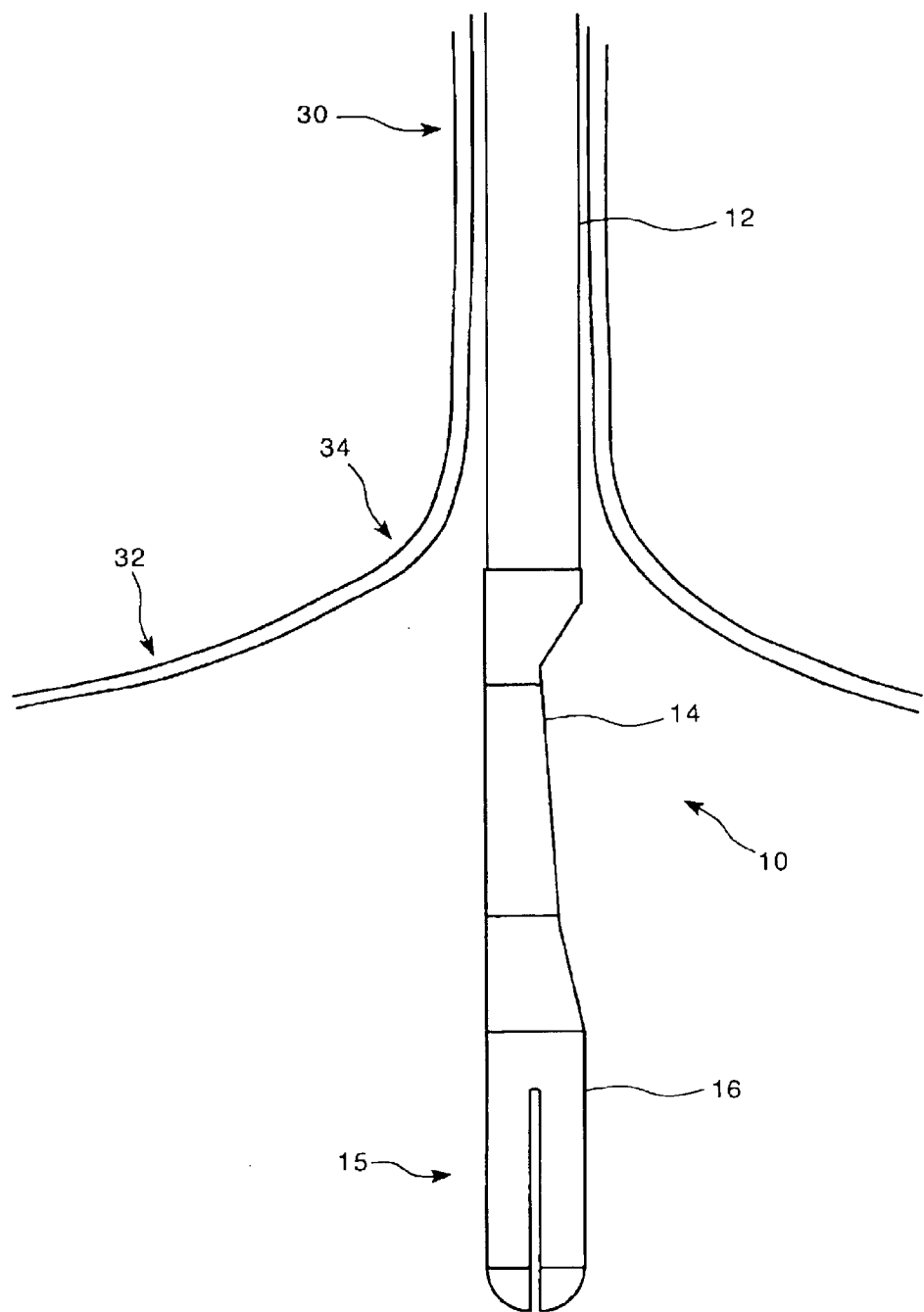
FIG. 1 is a side cross sectional view of a portion of an esophagus and a portion of a stomach, and a side view of an instrument in place in the esophagus and stomach.

The device consists of an instrument 10 with a proximal end (not shown), a shaft 12, a retroflexing portion 14, and a distal end effector 15 including movable arms 16, a retractor 20, and an implant 22. The function of the instrument is controlled by the user by controls at the proximal end, as is disclosed in the referenced patent applications. The device and method of the present invention will be illustrated using the accompanying drawings.

Figure 2:
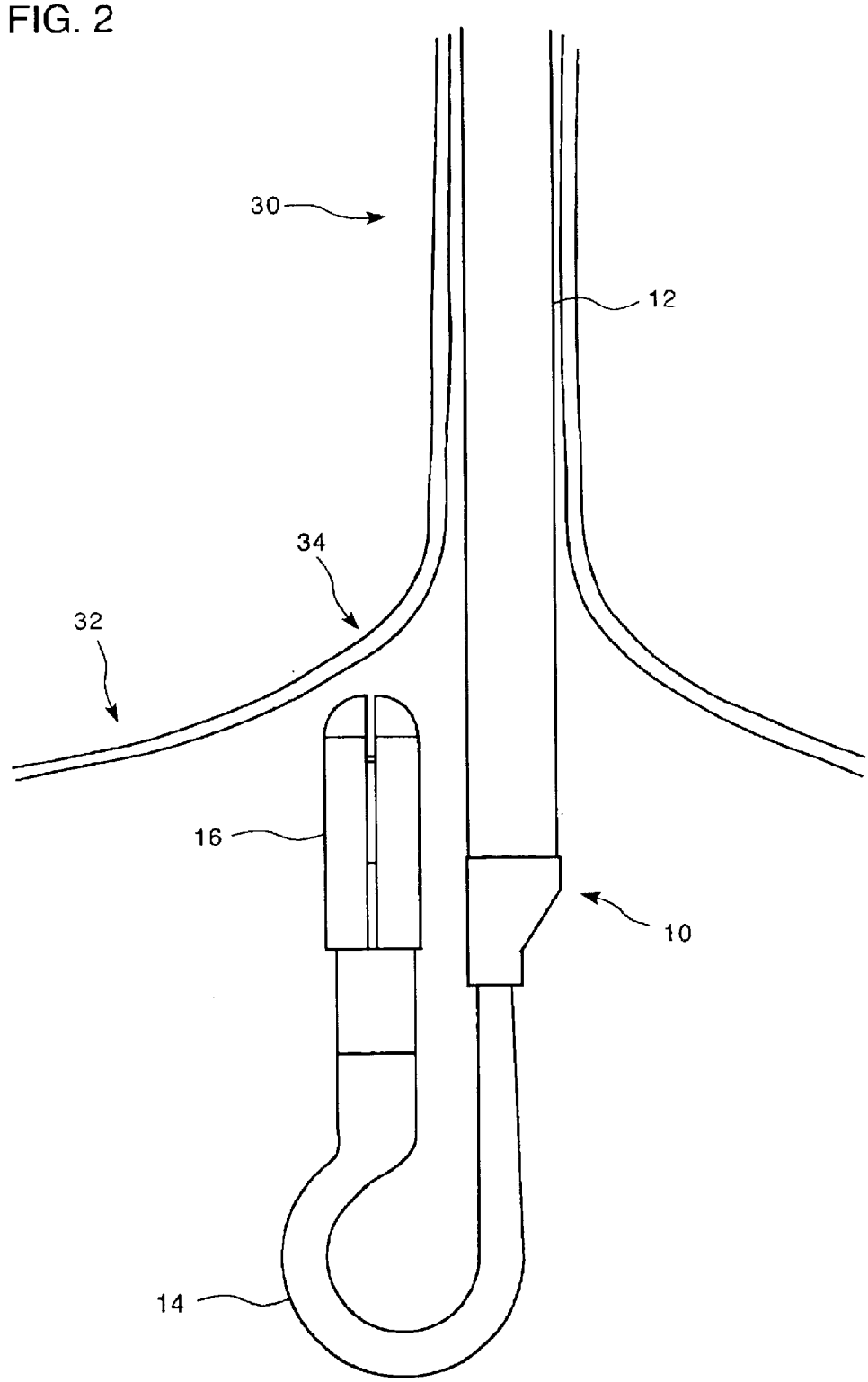
FIG. 2 is a side cross sectional view of a portion of the esophagus and a portion of the stomach, and a side view of the instrument in place in the esophagus and stomach, showing the instrument in a retroflexed position.

FIG. 1 shows the instrument 10 in place in the esophagus 30 and the stomach 32. The instrument is in a straight configuration, which is the configuration in which it is inserted into the esophagus and stomach FIG. 2 shows the instrument 10 in place in the esophagus 30 and the stomach 32, with the instrument 10 in a retroflexed position. Retroflexion of retroflexing portion 14 is accomplished as disclosed in the referenced patent applications. In this position, the distal end of the movable arms 16 of distal end effector 15 is located near the junction 34 of the esophagus 30 and the stomach 32.

Figure 3:
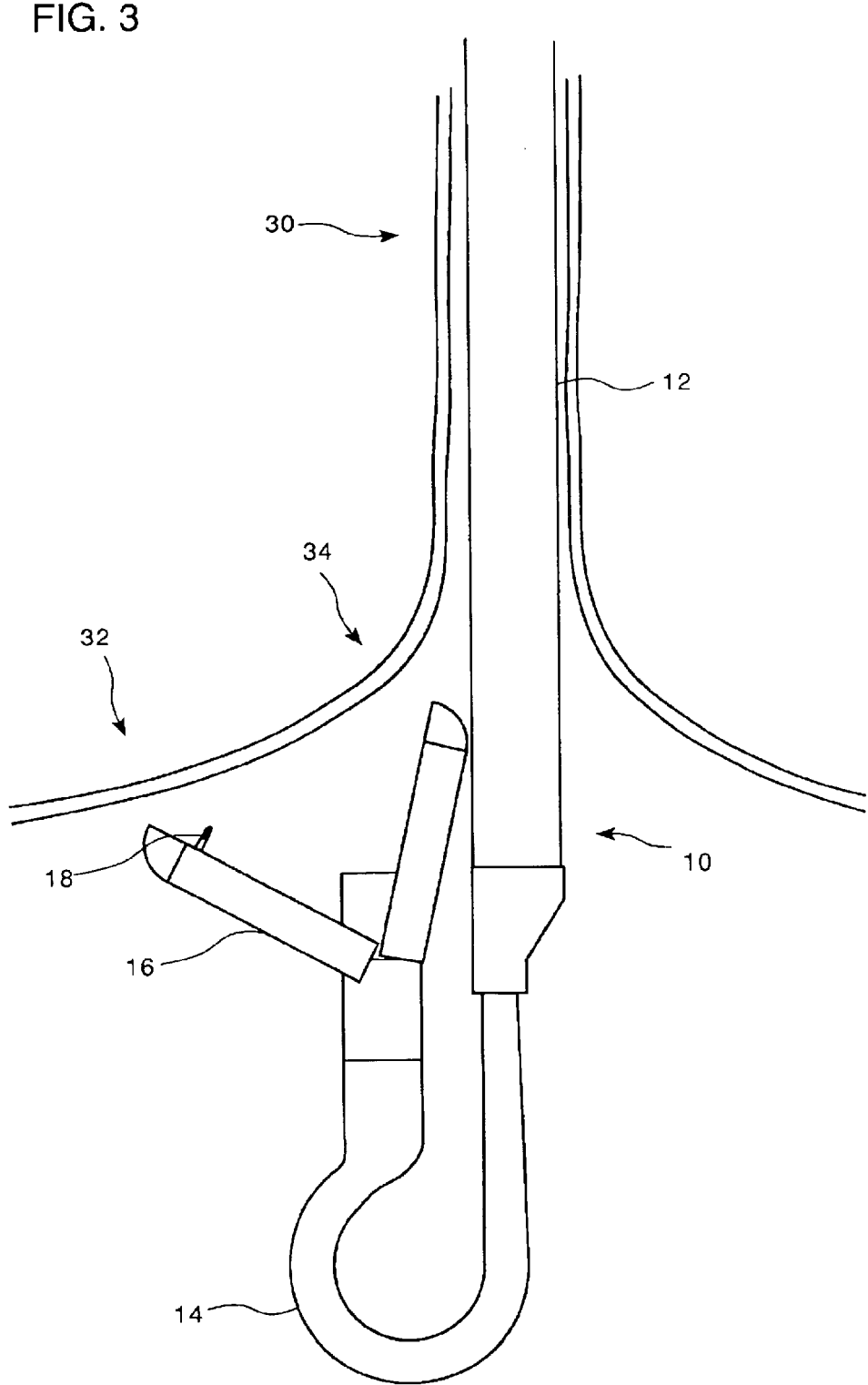
FIG. 3 is a side cross sectional view of a portion of the esophagus and a portion of the stomach, and a side view of the instrument in place in the esophagus and stomach, showing the movable arms open.
Figure 7:
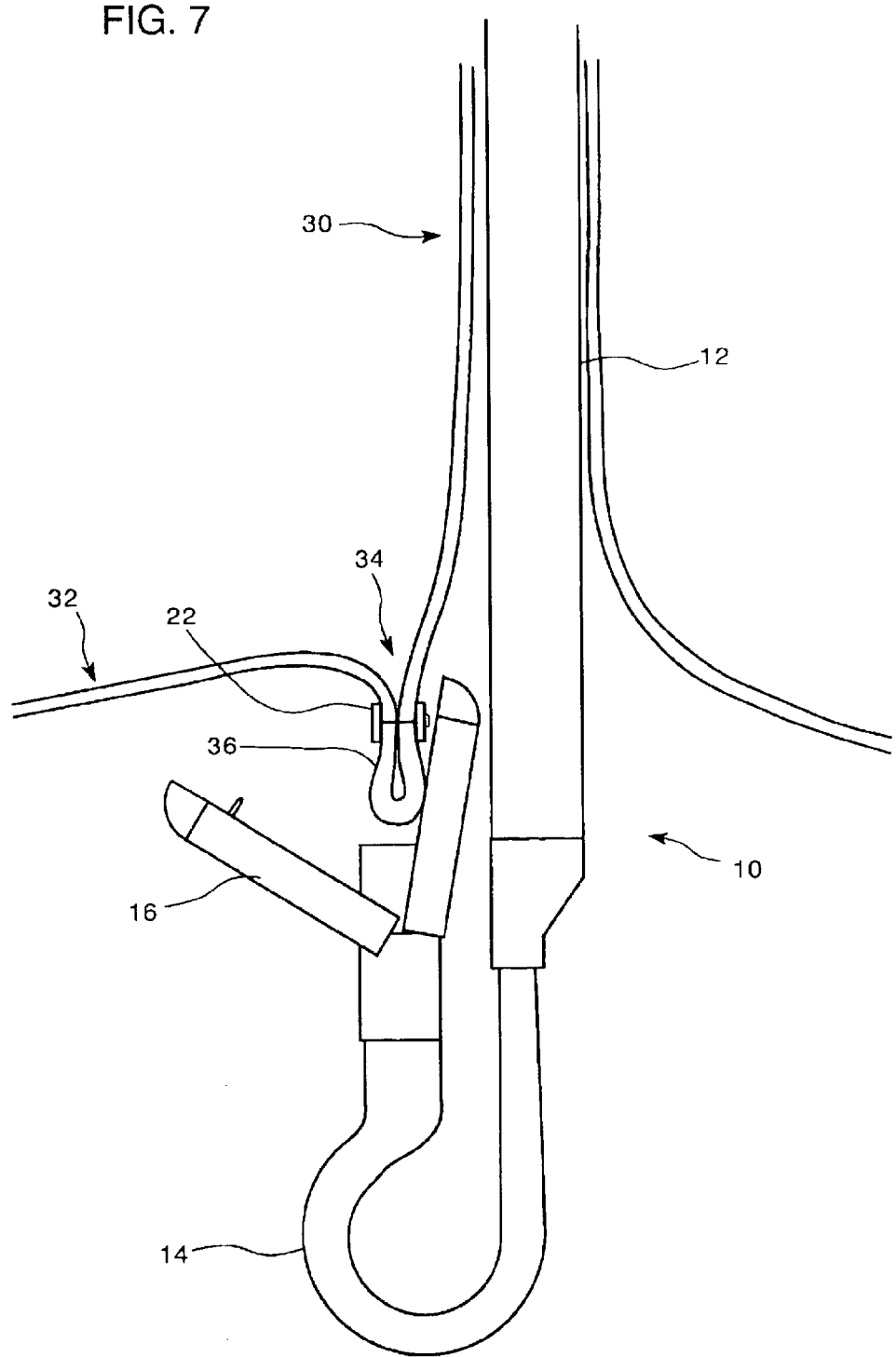
FIG. 7 is a side cross sectional view of a portion of the esophagus and a portion of the stomach, and a side view of the instrument in place in the esophagus and stomach, showing the movable arms open and an implant fixating the tissue fold.

FIG. 3 shows the instrument 10 in place in the esophagus 30 and the stomach 32, with the instrument 10 in a retroflexed position and the movable arms 16 in an open position revealing a portion 18 of an implant 22 (FIG. 7). It is important to note that the moveable arms 16 are oriented relative to the retroflexing portion 14 to grasp the tissue at the junction 34 of the esophagus 30 and the stomach 32. The movable arms 16 open and close in the same plane within which the retroflexing portion 14 moves. The actuating mechanism used to open movable arms 16 is substantially the same as the mechanisms used to actuate the medical instruments described in the U.S. patent application Ser. No. 09/859,579, entitled "TISSUE RECONFIGURATION," filed May 18, 2001, with the movable arms rotated 90° with respect to the configuration of the published application such that the arms 16 open and close in the same plane within which the retroflexing portion 14 moves.

Figure 4:
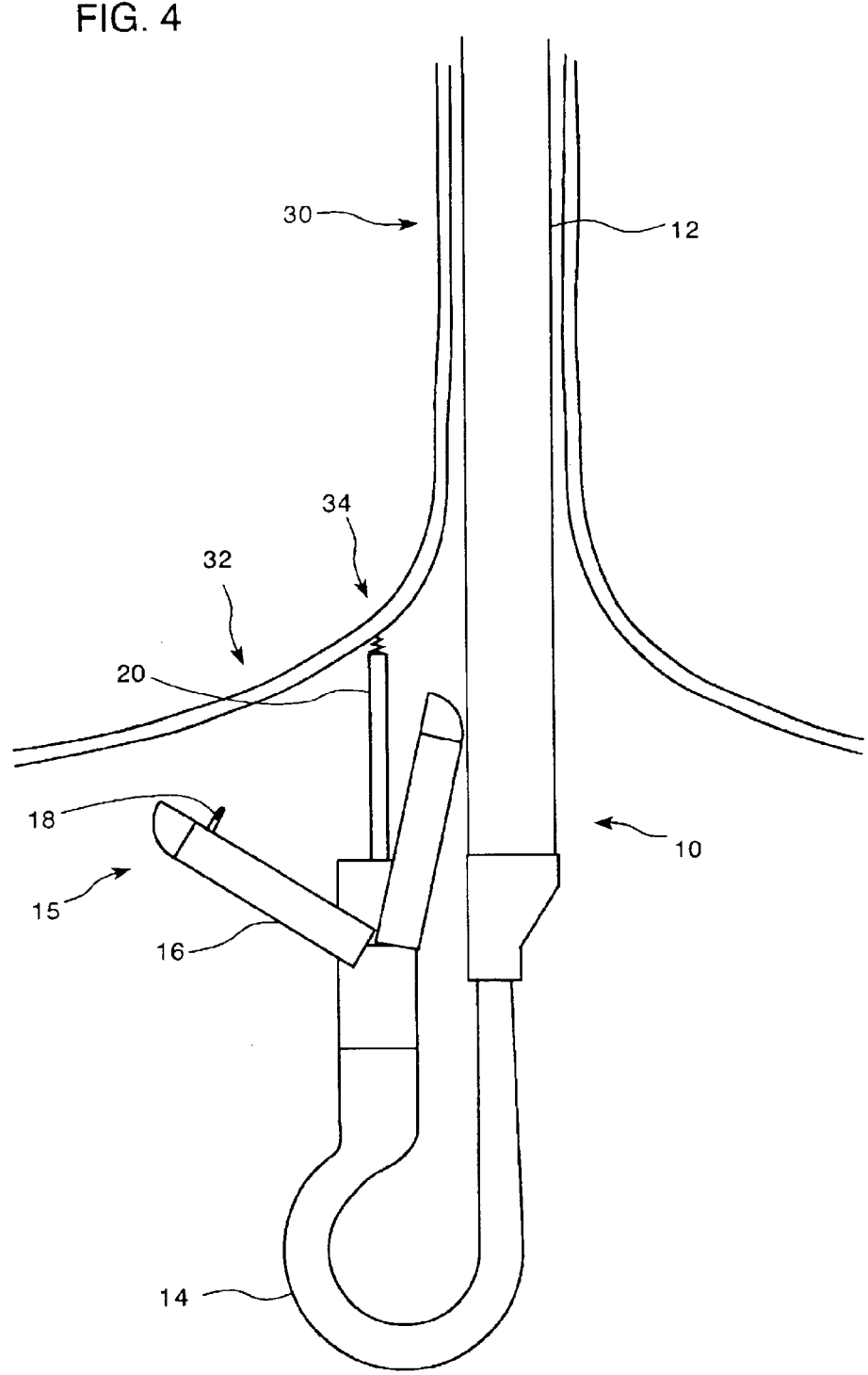
FIG. 4 is a side cross sectional view of a portion of the esophagus and a portion of the stomach, and a side view of the instrument in place in the esophagus and stomach, showing a retractor engaging tissue.

FIG. 4 shows the instrument 10 in place in the esophagus 30 and the stomach 32, with the instrument 10 in a retroflexed position, the movable arms 16 in an open position, and the retractor 20 engaged with the tissue at or near the junction 34 of the esophagus 30 and the stomach 32. Engagement of the retractor 20 with the tissue at or near the junction 34 is accomplished as is disclosed in the referenced patent applications.

Figure 5:
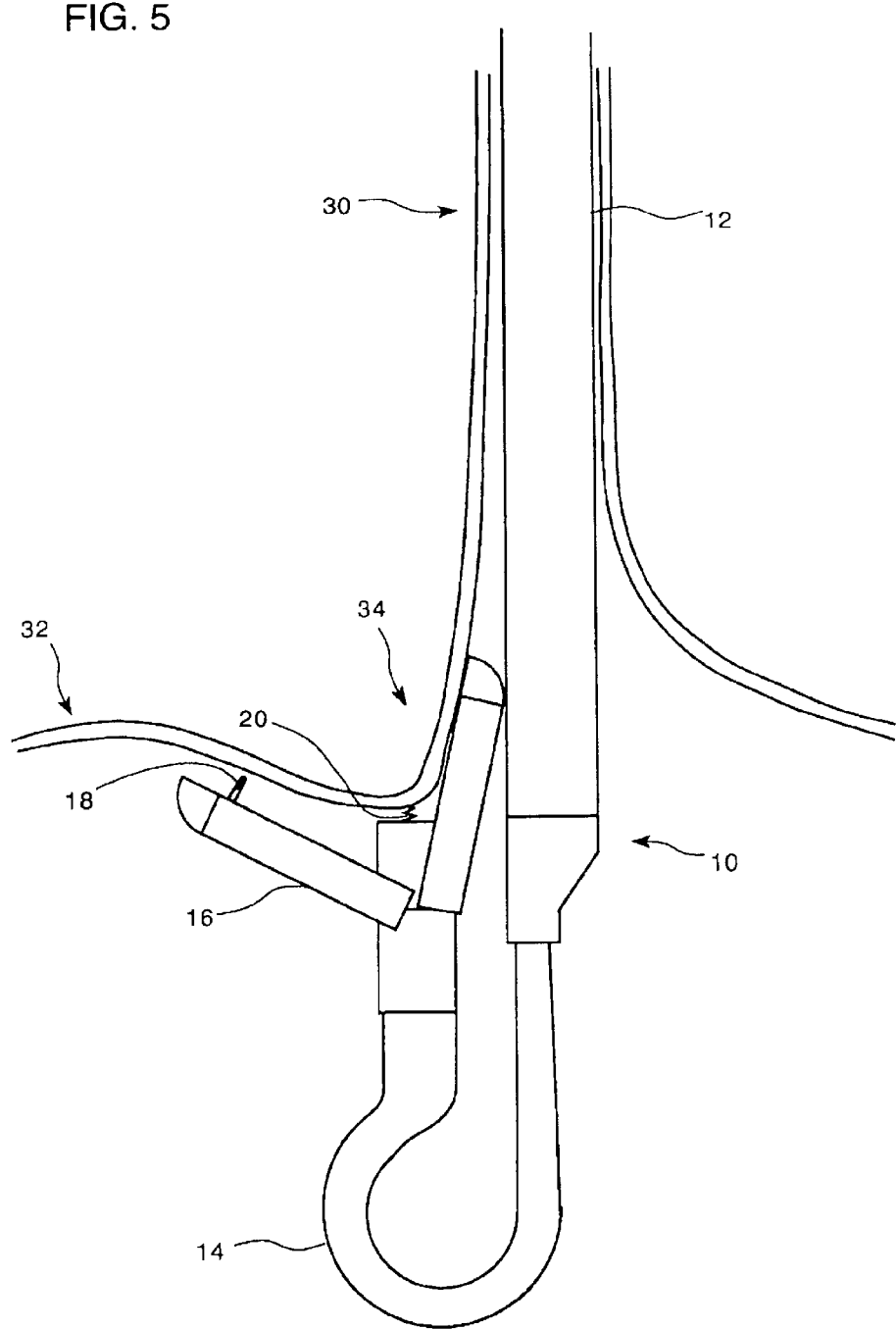
FIG. 5 is a side cross sectional view of a portion of the esophagus and a portion of the stomach, and a side view of the instrument in place in the esophagus and stomach, showing the retractor retracting the tissue.

FIG. 5 shows the instrument 10 in place in the esophagus 30 and the stomach 32, with the instrument 10 in a retroflexed position, the movable arms 16 in an open position, and the retractor 20 retracting the tissue at or near the junction 34 of the esophagus 30 and the stomach 32 into the space between the movable arms 16.

Figure 6:
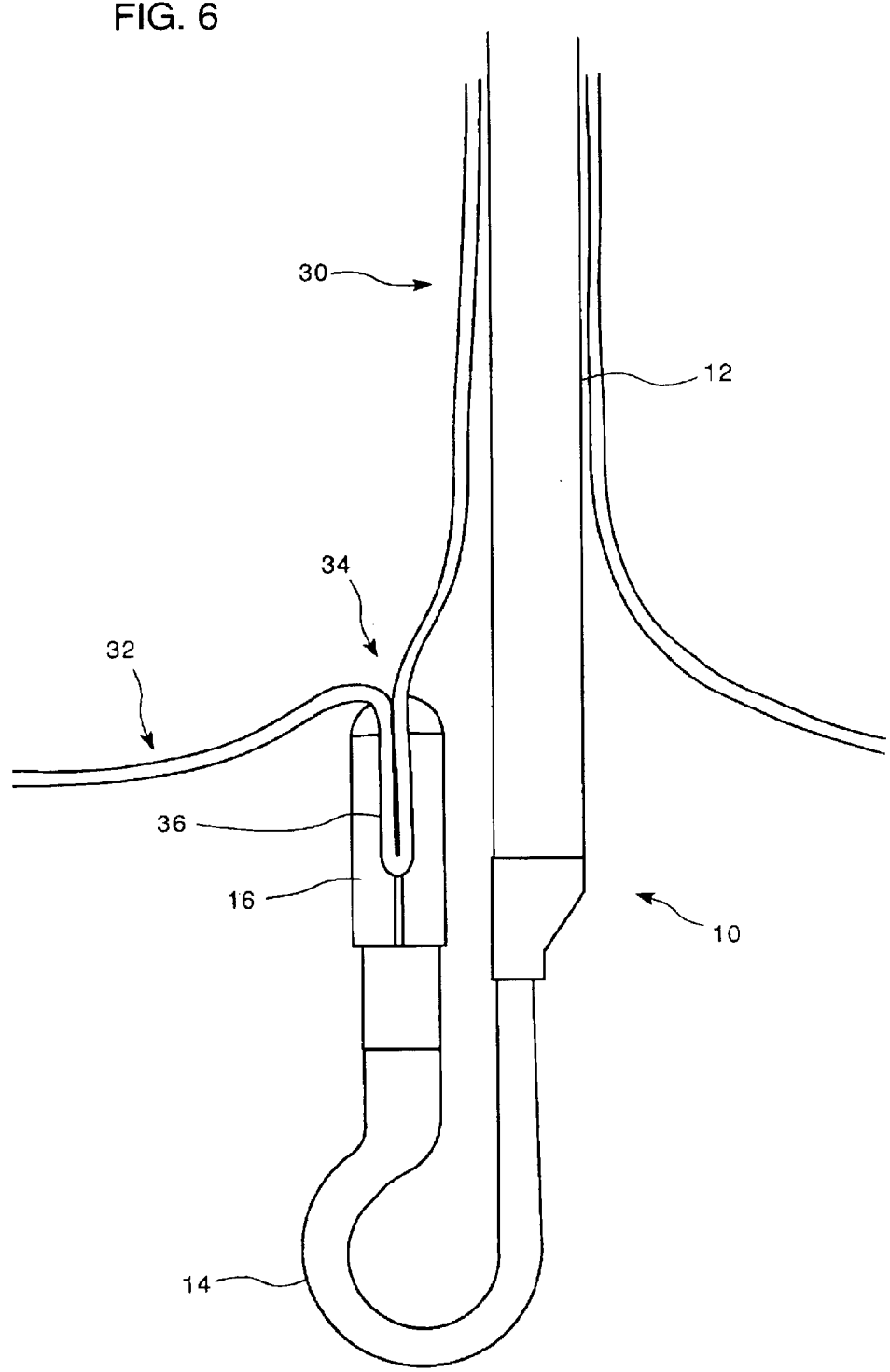
FIG. 6 is a side cross sectional view of a portion of the esophagus and a portion of the stomach, and a side view of the instrument in place in the esophagus and stomach, showing the movable arms closed, forming a tissue fold.

FIG. 6 shows the instrument 10 in place in the esophagus 30 and the stomach 32, with the instrument 10 in a retroflexed position, and the movable arms 16 closed, to create a fold 36 of tissue at or near the junction 34 of the esophagus 30 and the stomach 32. The mechanism to close movable arms is as is disclosed in the referenced patent applications.

FIG. 7 shows the instrument 10 in place in the esophagus 30 and the stomach 32, with the instrument 10 in a retroflexed position, and the movable arms 16 opened. An implant 22 has been placed through the tissue to maintain fixation of the tissue fold 36. Placement of the implant is accomplished as is disclosed in the referenced patent applications.

Figure 8:
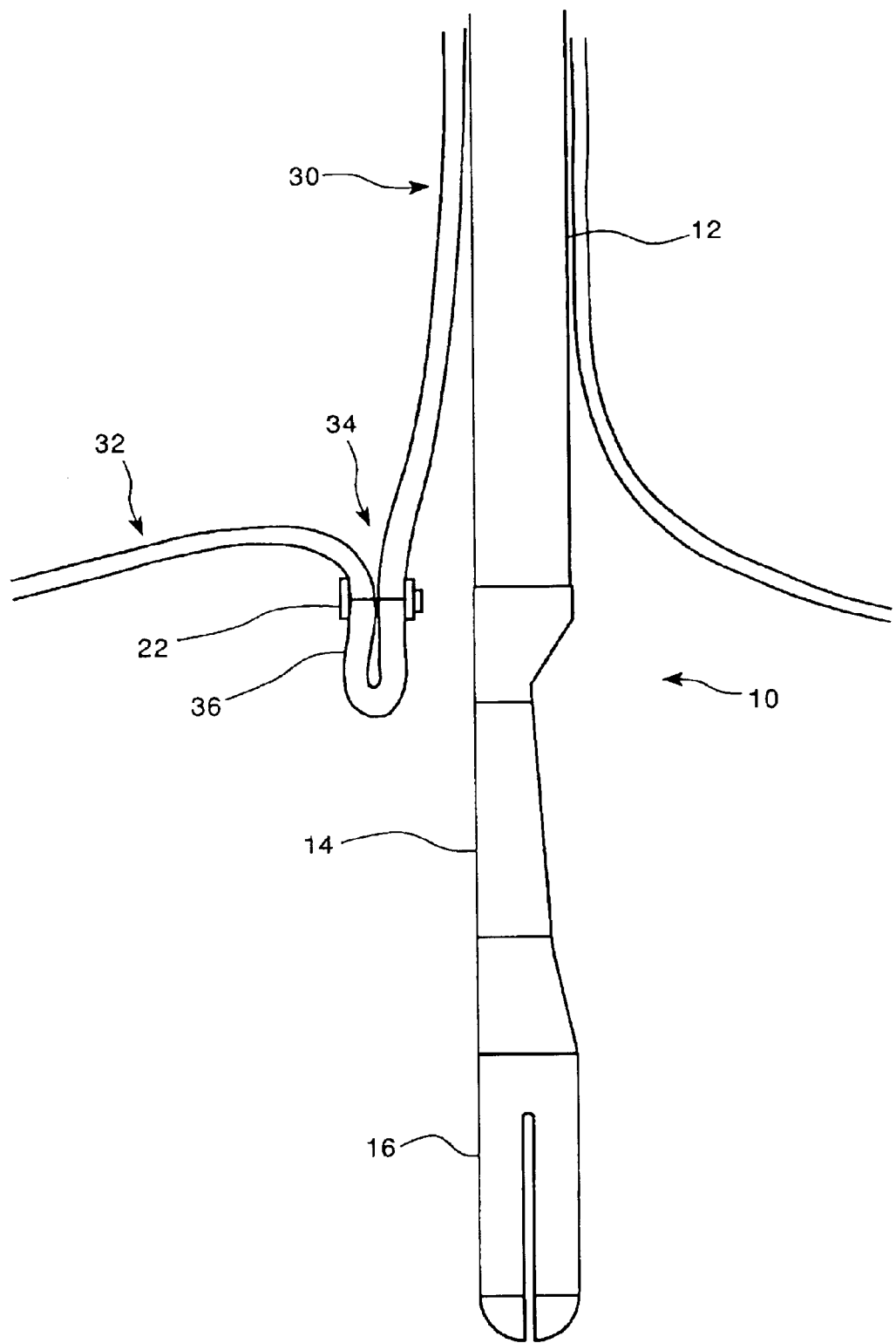
FIG. 8 is a side cross sectional view of a portion of the esophagus and a portion of the stomach, and a side view of the instrument in place in the esophagus and stomach, showing the tissue fold, with the instrument in a straight configuration for removal from the patient.

FIG. 8 shows the instrument 10 in place in the esophagus 30 and the stomach 32, with the instrument 10 in a straight position, and the movable arms 16 closed. The tissue fold 36 is shown, fixated by implant 22. The instrument 10 is in position for removal from the patient.

This invention provides a device and method which can be used to treat GERD by creating and fixating a fold of tissue at or near the junction of the esophagus and the stomach, thereby fixating the wall of the stomach to the wall of the esophagus. This invention allows this fold to be created and fixated via a completely endoluminal technique.

In another aspect of the invention, more than one fold is created in the tissue at or near the junction of the esophagus and the stomach.

In another aspect of the invention, the movable arms are attached to the retroflexing portion in a manner that allows the operator to rotate the position of the movable arms relative to the retroflexing portion about the center axis of the movable arms, thus allowing the operator to vary the orientation of the tissue fold.

While the invention has been described in detail with reference to the preferred embodiments thereof, it will be apparent to one skilled in the art that various changes and modifications can be made and equivalents employed, without departing from the present invention. For example, in the embodiment described above in conjunction with FIGS. 1–8, the moveable arms open and close in the same plane within which the retroflexing portion moves. However, it is appreciated that the plane in which the moveable arms open and close relative to the retroflexing portion can be at other orientations including angles between the same plane (i.e., 0°) and a plane transverse (i.e., 90°) to the plane within which the retroflexing portion moves. Indeed, in certain embodiments, the medical instrument can include a mechanism for allowing the user to adjust the angle of the moveable arms relative to the retroflexing portion.

What is claimed is:

1. A method comprising:

advancing an apparatus including an elongated member transorally into the stomach, the apparatus including a distal end effector having first and second members configured to engage tissue, the first and second members being movable relatively toward one another generally in a first plane, and moving the distal end effector relative to the elongated member in the first plane such that the distal end effector is retroflexed out of alignment with the elongated member to position the first and second members for engagement with the tissue, at least one of the first and second members carrying a fixation device for securing engaged portions of tissue together.

2. The method of claim 1 further comprising engaging tissue by moving the first and second members relatively toward one another generally in the first plane.

3. The method of claim 2 wherein the moving of the first and second members engages a first tissue section with a first securing part of the fixation device and a second tissue section with a second securing part of the fixation device.

4. The method of claim 1 further comprising piercing the tissue with a third member of the distal end effector prior to engaging the tissue with the first and second members.

5. The method of claim 1 further comprising releasably mounting the first and second members to the distal end effector.

6. The method of claim 1 further comprising removing the first and second members from the distal end effector.

7. The method of claim 6 further comprising releasably mounting third and fourth members on the distal end effector, at least one of the third and fourth members carrying a fixation device for securing engaged portions of tissue together.

8. The method of claim 1 wherein at least one of the first and second members pierces the tissue.

9. The method of claim 1 further comprising separating a frangibly coupled part of the fixation device from at least one of the first and second members.

10. The method of claim 9 wherein the first and second members interact to separate the frangibly coupled part.

11. The method of claim 1 further comprising securing the engaged portions of tissue with the fixation device.

12. The method of claim 1 further comprising providing the first member with a first distal tip releasably mounted to the first member, and the second member with a second distal tip releasably mounted to the second member, at least one of the first and second distal tips carrying the fixation device.

13. The method of claim 12 further comprising releasably mounting the first distal tip on the first member and releasably mounting the second distal tip on the second member.

14. The method of claim 12 further comprising removing the first distal tip from the first member and removing the second distal tip from the second member.

15. The method of claim 14 further comprising releasably mounting a third distal tip on the first member and releasably mounting a fourth distal tip on the second member, at least one of the third and fourth distal tips carrying a fixation device for securing engaged portions of tissue together.

* * * * *